United States Patent [19]

Schrader

[11] Patent Number: 5,534,997
[45] Date of Patent: Jul. 9, 1996

[54] RAMAN SPECTROMETER USING A REMOTE PROBE WITH ENHANCED EFFICIENCY

[75] Inventor: Bernhard Schrader, Essen-Heisingen, Germany

[73] Assignee: Bruker Analytische Messtechnik GmbH, Rheinstetten, Germany

[21] Appl. No.: 309,000

[22] Filed: Sep. 20, 1994

[30] Foreign Application Priority Data

Jul. 15, 1994 [DE] Germany .............................. 9411467 U

[51] Int. Cl.$^6$ ................................................ G01N 21/65
[52] U.S. Cl. ................................................ 356/301; 385/12
[58] Field of Search ................................. 356/73.1, 301; 385/12; 250/227.18, 227.23

[56] References Cited

U.S. PATENT DOCUMENTS

| | | |
|---|---|---|
| 4,029,391 | 6/1977 | French .............................. 250/227.23 X |
| 4,533,243 | 8/1985 | Zhukov et al. ..................... 385/12 X |
| 5,112,127 | 5/1992 | Carrabba et al. ................... 356/301 |
| 5,243,410 | 9/1993 | Larson et al. ...................... 250/228 X |
| 5,261,410 | 11/1993 | Alfano et al. ...................... 356/301 X |

Primary Examiner—Vincent P. McGraw

[57] ABSTRACT

The invention relates to a Raman spectrometer connected by a bundle of optical fibers with an external probe to be attached on the surface of the sample with a laser beam for the excitation of Raman radiation within the sample with the laser radiation transported to the sample by one or several central optical fibers and with a collecting element which collects the Raman radiation of the sample and sends it through the optical fiber bundle to a Raman spectrometer to be analyzed. Upon the end of the optical fiber bundle different collecting elements may be attached with the transparent optical elements having the shape of a cylinder, a paraboloid or a truncated sphere. Thus, the spectrometer can be simply adapted to different samples for optimal collection of Raman light.

21 Claims, 3 Drawing Sheets

RAMAN SPECTROMETER USING A REMOTE PROBE WITH ENHANCED EFFICIENCY

BACKGROUND OF THE INVENTION

The invention is concerned with the analysis of a remote sample by Raman spectroscopy, particularly for medical diagnostics. Raman scattering is extremely weak. In order to record laser-excited Raman spectra of delicate remote samples in a limited time one has to design a probe with maximum efficiency. The conversion of the laser radiation into Raman radiation should be as complete as possible and the probe has to collect the Raman radiation with a minimum of losses. At the same time heating of the sample by the absorbed laser radiation should be at a minimum in order not to denature the sample.

Such a probe allows the investigation of samples which cannot be brought into the spectrometer. Due to the low intensity of the Raman effect it is desirable to transmit a large radiant power of the laser radiation to the sample without endangering it and to collect the Raman radiation and transport it to the spectrometer as completely as possible. The contamination or pollution of the part of the probe which has been in contact with the (biological) sample should be removable by simple exchange, allowing cleaning as well as sterilizing. The exchangeable part of the probe should allow matching to different kinds of samples. The usual Raman spectrometers do not allow this.

Raman spectrometers with optical fiber bundles for the examination of remote samples are already on the market. Existing Raman spectrometers are for example connected to the sample by an optical fiber bundle without any coupling element or with a positive lens imaging Raman radiation from the sample into the optical fiber bundle.

It is the aim of the invention to provide a Raman spectrometer with an exchangeable probe that improves the figure of merit of existing Raman spectrometers.

SUMMARY OF THE INVENTION

The invention solves this problem by using a probe with a transparent optical element made of glass, quartz or sapphire with a first planar surface which is in contact with the planar end surface of the optical fiber bundle or is imaged upon it, with a second surface which may be brought in direct contact with the sample, and with a third lateral surface surrounding the collecting element. The third surface may be totally reflecting or be covered with a reflecting surface. The transparent optical element is the essential part of a collecting element which may be attached upon the optical fiber bundle or detached from it.

Preferably, the Raman spectrometer is of the FTIR (Fourier transform infrared) type. However, it can be of any other type, e.g. a grating spectrometer.

Ray tracing calculations yielded optimum designs of the transparent optical element that selects a definite surface area on the sample which is illuminated by the laser and enables the optimum collection of the Raman radiation. The figure of merit may be thus enhanced by one order of magnitude compared to an optical fiber bundle without such collecting element. The detachability makes it possible to remove, clean, sterilize or exchange the collecting element, which is the only part in contact with the sample.

Preferably the third lateral surface of the transparent optical element may be glued into a tube, the inner diameter of which is nearly equal to the diameter of the optical fiber bundle and the first surface of the transparent optical element. Thus the tube containing the transparent element is exchangeable as a unit, it is the collecting element of the probe.

This gives the advantage of a compact and robust exchangeable element enabling routine investigations of different samples with different collecting elements.

The length of the optical fiber bundle is preferably about 2 meters.

This length gives for many applications, for instance in the field of medical diagnostics, an optimal compromise between short light paths within the optical fiber and the flexibility of the probe to be brought to the sample, e.g. the skin of patients.

The diameter of the optical fiber bundle is, depending on the type of the spectrometer, between 0.5 to about 10–12 mm.

This diameter enables a large optical conductance of the probe equal to the optical conductance of the spectrometer, in order to allow recording spectra with an acceptable signal/noise ratio within relatively short times.

Preferably laser radiation in the near infrared range is employed to excite the Raman spectra.

Though the intensity of the Raman radiation is approximately proportional to the fourth power of the frequency of the exciting radiation, which would make the use of UV laser radiation desirable, exciting radiation in the near infrared range is preferably used, because it allows Raman spectra of nearly any sample to be obtained without interference of fluorescence from ubiquitous normal components of the sample or of impurities. In addition, light absorption is at a minimum in the near infrared for fibers produced of fused silica.

Between the end surface of the optical fiber bundle and the first surface of the transparent optical element an immersion liquid can be added in order to minimize radiation losses due to reflection at the surfaces.

Some embodiments of the invention have optical fibers for the laser and the Raman radiation with separated end surfaces which are imaged onto the first surface of the transparent element by lenses or mirrors.

If the exchangeable collecting unit has to be sterilizable, it should not contain components which may be damaged by the sterilization process.

This exchangeability is especially advantageous for applications in medical diagnostics or biological investigations where the part of the probe which has been in contact with the sample may be made aseptic and may be employed again without contaminating the next sample or a patient.

The refractive index of the transparent optical element is preferably in the range 1.4 to 1.9. In this range materials are commercially available which may be worked easily like quartz, glass, sapphire whose focusing properties may be easily optimized.

The optical fiber bundle is preferably of the Y-type. One or several central optical fibers are separated—beginning at the planar end surface of the bundle—from the other fibers. The laser radiation is transported to the sample through these fibers, while the other fibers transport the Raman radiation to the spectrometer.

The word 'central' should not be understood too strictly, non-central or arrangements with mixed laser and Raman fibers are possible. There are also embodiments where the laser and Raman fiber bundles stay separated although the optical paths meet (see FIG. 6 and related part of the specification).

The Y-type arrangement has the advantage that the laser and the Raman radiation may be managed independently.

The laser radiation excites a typical Raman spectrum of the optical fibers on its way from the laser to the sample. This may be removed by inserting an optical filter, e.g. an interference filter near the end of the optical fiber. The interference filter may preferably be inserted between a pair of fiber coupling spheres or GRIN (GRadient INdex) lenses.

The optical fiber bundle is preferably produced from pure (synthetic) fused silica.

This material has large transmittance in the near infrared range and produces a minimum of interfering Raman or fluorescence radiation or Rayleigh or Mie scattering.

Preferable embodiments have a press-button switch at the probe to switch on the laser or to operate a shutter on the laser.

Thus, the unintentional emission of visible or invisible laser radiation can be avoided, which otherwise may endanger persons or destroy a sample.

A specially preferable embodiment includes a gravity-sensitive switch which opens the laser beam only when the beam is aimed downwards. This largely prevents irradiation of the eyes of persons in the neighborhood of the sample. Additionally, all persons in the neighborhood of the spectrometer have to wear safety glasses and to stay at an eyesafe distance.

A first embodiment of the transparent element is a truncated cone with the smaller diameter at the sample surface. This allows collection of Raman radiation which leaves the sample in an angle which is larger than the collecting angle of the optical fibers.

As a special case the transparent element is a right circular cylinder.

This especially easy to produce element allows the irradiation of a surface of the sample with the same diameter as the optical fiber bundle and the collection of the Raman radiation from the same surface area. Thus the exciting laser radiation is not tightly focused; it allows collection of sufficient Raman intensity without denaturization or pyrolysis of a sample.

The ratio of the length of the cylinder to its diameter is of the order of 1 allowing optimal adaptation of the probe to the sample.

Another embodiment of the transparent element is a paraboloid.

It allows the investigation of the Raman spectra of sample areas having a diameter somewhat smaller (about $1/3$ to $1/7$) than the diameter of the optical fiber bundle. This element acts as a cross-section transformer which collects Raman radiation emitted within a solid angle of about $2\pi$ steradians and sends it through the optical fiber bundle within the acceptable solid angle. The surface area of the paraboloid near the sample can be pressed somewhat into the surface of the sample (e.g. human skin) enhancing the optical contact of the sample with the collecting element.

As a variant of this embodiment the tip of the paraboloid is truncated which ensures a better contact with non-deformable surfaces of a sample.

Preferably the distance between the firsts planar surface of the paraboloid to the tip is about 2 times the diameter of the first surface.

This distance optimizes the figure of merit with a reduced illuminated area.

In a third embodiment the transparent element is a truncated sphere with two parallel planar truncations. The larger planar surface is brought into contact with the sample. The smaller planar surface with a surface area equal to that of the optical fiber bundle, ensures the contact with the optical fiber bundle. Preferably the larger surface contains the center of the sphere.

Thus, surface areas may be investigated which are somewhat larger than the area of the optical fiber bundle. Raman radiation which leaves the sample at an angle that cannot be transported through the optical fiber bundle is reflected back to the sample. Thus, the reflecting layer upon the surface of the sphere acts, together with the surface of the sample, as a multireflecting unit for the exciting as well as the Raman radiation, enhancing the figure of merit by about one order of magnitude when compared with the arrangement without the surface mirror.

In other embodiments the transparent elements are not produced from massive material but rather they may be hollow elements with the third surface constructed from cylindrical, conical, parabolic or spherical mirrors. The transparent element does not have planar surfaces, they are given by the sample and/or the end surface of the optical fiber bundle. The refractive index within this element is that of air, which has to be taken into account when the optical properties of the transparent element are being calculated. Paraboloids can only be used as hollow elements when their tips are truncated.

Especially preferable is a Raman spectrometer as described which is equipped with at least three different exchangeable collecting elements, the transparent parts of which have the form of a cylinder, a paraboloid or a truncated sphere.

Thus, the collecting element may be exchanged quickly and easily in order to adapt it to a sample of different size and quality.

Other advantages of the invention are given by the description and the figures. The described characteristics may be employed singly or in combination. The descriptions give examples, they do not describe all possible embodiments, they are described additionally by concrete examples of employment in the following paragraphs.

DESCRIPTION OF THE PREFERRED EMBODIMENTS

Figure 1:
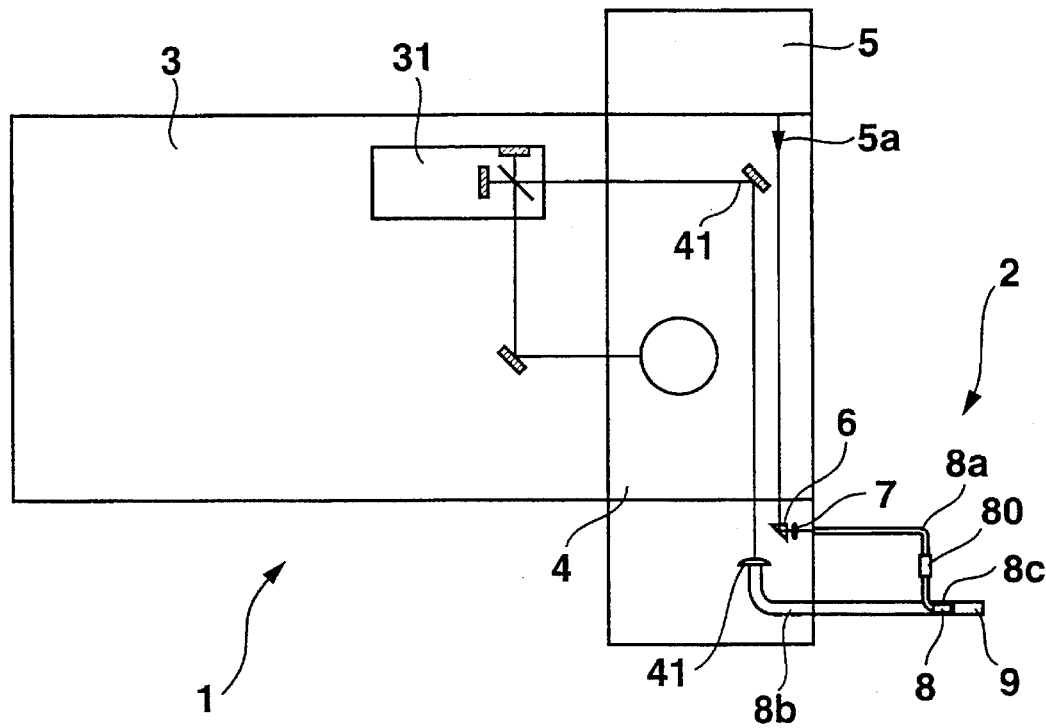
FIG. 1 shows a scheme of a Raman spectrometer with an external remote probe.

The invention is concerned with the enhancing of the efficiency of all types of Raman spectrometers with remote probes. For example, in FIG. 1 a schematic diagram of a Raman spectrometer 1 with an external remote probe 2 is shown. The spectrometer 1 is realized as conventional Fourier-transform infrared- (FTIR-) spectrometer in a housing 3 connected to a Raman attachment 4. Here, as example, the spectrometer IFS 66 with Raman module FRA 106 of BRUKER Analytische Messtechnik GmbH, Rheinstetten, Germany, is sketched. Details of the spectrometer are not given, they are well known. A Nd:YAG laser 5 is attached to the Raman module for the excitation of the Raman radiation. The laser radiation 5a is directed via a prism 6 and a lens 7 within the Raman module to the central optical fiber(s) 8a of an optical fiber bundle 8. For the elimination of the undesired Raman radiation excited within this (these) fiber(s) 8a an optical filter is introduced which isolates the exciting radiation. The central optical fiber(s) 8a combined with another optical fiber bundle 8b constitute an optical fiber bundle 8 of the Y type, this means the bundles 8a and 8b assemble to an integrated bundle 8. The central optical fiber needs not be situated, as already discussed, exactly in the center. Upon the planar end 8c of the joint optical fiber bundle 8 a transparent element 9 is attached for collecting of the laser light 5a as well as for guiding the collected Raman radiation (not shown) to the optical fibers of the bundle 8b. The optical fiber bundle 8 and the collecting element 9 constitute the external probe 2.

Figure 2:
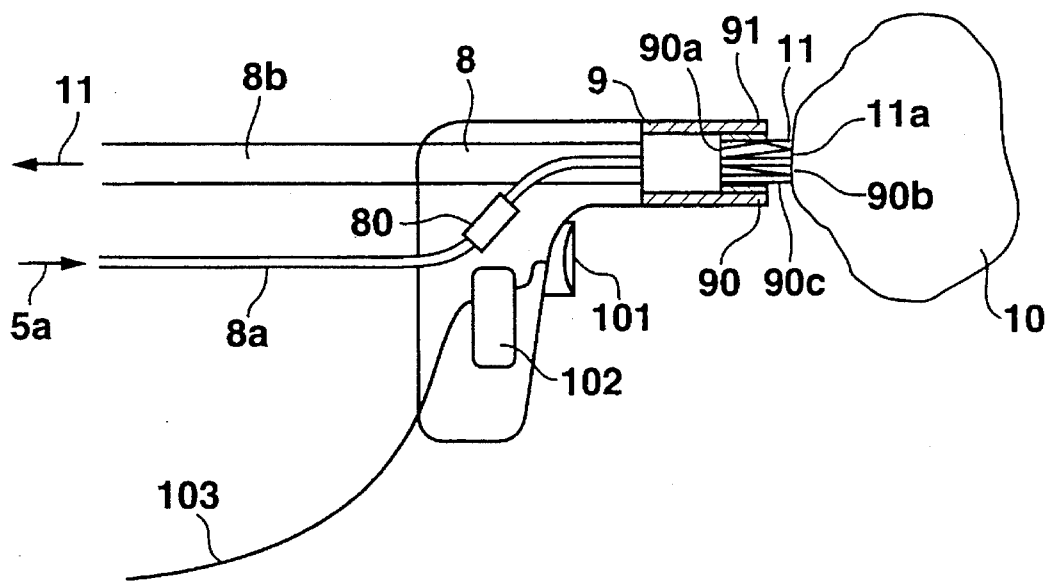
FIG. 2 shows an external remote probe with a collecting element having a cylindrical transparent element.

FIG. 2 shows a first embodiment of the external probe 2 of the Raman spectrometer 1 in detail. The optical fiber bundle 8 contains a central optical fiber 8a for the laser light 5a as well as surrounding fibers 8b for the transport of the Raman radiation 11 emitted by a sample 10 to the Raman spectrometer. At the sample (or collecting element) end of the optical fiber bundle 8 a handle is attached with two switches, 101 and 102. The first one, 101 is a press-button switch activated by hand; the other, 102, is a gravity-sensitive switch. Both switches in combination activate, as described above, the laser radiation 5a by the electrical connection 103.

A collecting element 9 is attached upon the circular end of the optical fiber bundle 8. The collecting element 9 consists of a transparent optical element 90, for this example of cylindrical shape. The cross-sectional area of the cylinder 90 corresponds to that of the optical fiber bundle 8. When attached, the end surface 90a of the cylinder 90 is in contact with the planar end surface of the optical fiber bundle 8. The contact may be improved by an immersion fluid. The lateral surface 90c of the cylinder 90 may be covered with a mirror or used as total reflecting element when it is inserted in a hollow-cylindrical support 91. The support 91 is attached to the end of the optical fiber bundle 8. The laser light 5a, transported by the optical fiber 8a emerges from the end of the optical fiber bundle 8 as diverging beam into the transparent optical element 90 and leaves it at the second surface 90b of the cylinder 90 to illuminate the surface 11a of the sample 10. Raman radiation 11 emerging from the sample 10 at different angles into the transparent element 90 may be reflected at the lateral surface 90c, it enters the optical fiber bundle 8 through the end surface 90a, and is transported by it to the spectrometer 3. This cylindrical form of the element 90 is especially suitable for the investigation of medium-sized areas of the sample 10.

An optical filter 80 is inserted in the central optical fiber 8a. It is described in connection with FIG. 7.

Figure 3:
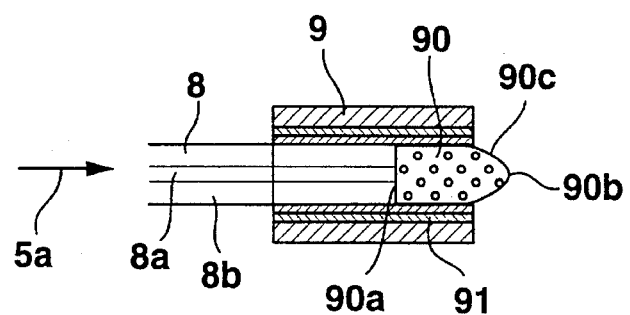
FIG. 3 shows a collecting element with a paraboloid as transparent element.

FIG. 3 shows another embodiment of the invention. For clarity, in comparison with FIG. 2, the switches are not shown. The other elements and their reference numbers correspond to those of FIG. 2. However, the transparent element 90 does not have the form of a cylinder; it has now the form of a paraboloid. Thus its lateral surface 90c is curved in two directions. It is covered with a reflecting layer with the exception of the sample-contacting area 90b which assumes the function of the planar surface 90b of the cylinder 90 in FIG. 2. This embodiment is especially useful for the investigation of small surface areas of the sample 10. It may even be impressed into the sample.

Figure 4:
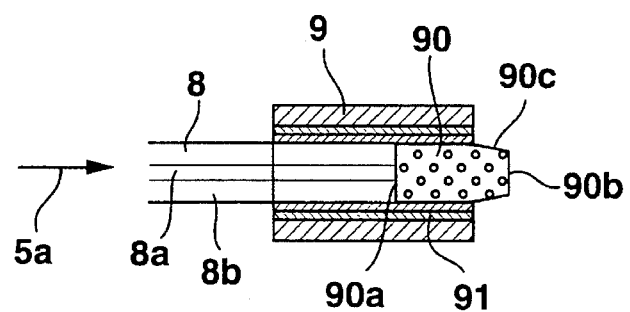
FIG. 4 shows a collecting element with a truncated paraboloid as transparent element.

FIG. 4 shows another embodiment of the invention. For clarity, in comparison with FIG. 2, the switches are not shown. The other elements and their reference numbers correspond to those of FIGS. 2 and 3. The transparent element 90 does not have the form of a complete paraboloid; its tip is cut off to give a planar surface 90b. Its lateral surface 90c is covered with a reflecting layer. There is, as in FIG. 2, a planar surface 90b, however, the diameter of it is reduced. This embodiment is especially useful for the investigation of small areas of samples with a hard planar surface.

Figure 5:
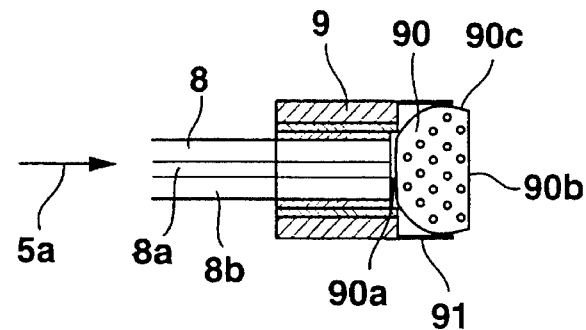
FIG. 5 shows a collecting element with a truncated sphere as transparent element.

FIG. 5 shows another embodiment of the invention. For clarity, in comparison with FIG. 2 the switches are not shown. The other elements and their reference numbers correspond to those of FIGS. 2 and 3. The transparent element 90 now has the form of a truncated sphere. Its lateral area 90c is now spherical and covered with a reflecting layer. The large planar surface 90b of the truncated sphere corresponds to the planar surface 90b of the cylinder 90 in FIG. 2. This embodiment is especially useful for the investigation of larger areas of the surface of the sample 10.

As discussed above, the transparent elements of FIGS. 2, 3, 4, and 5 may be hollow rotationally-symmetric reflecting elements. The lateral surfaces 90c are now the inner surfaces of hollow mirrors. The end surfaces are now virtual, they are the axial limiting surfaces of the reflecting elements.

Figure 6:
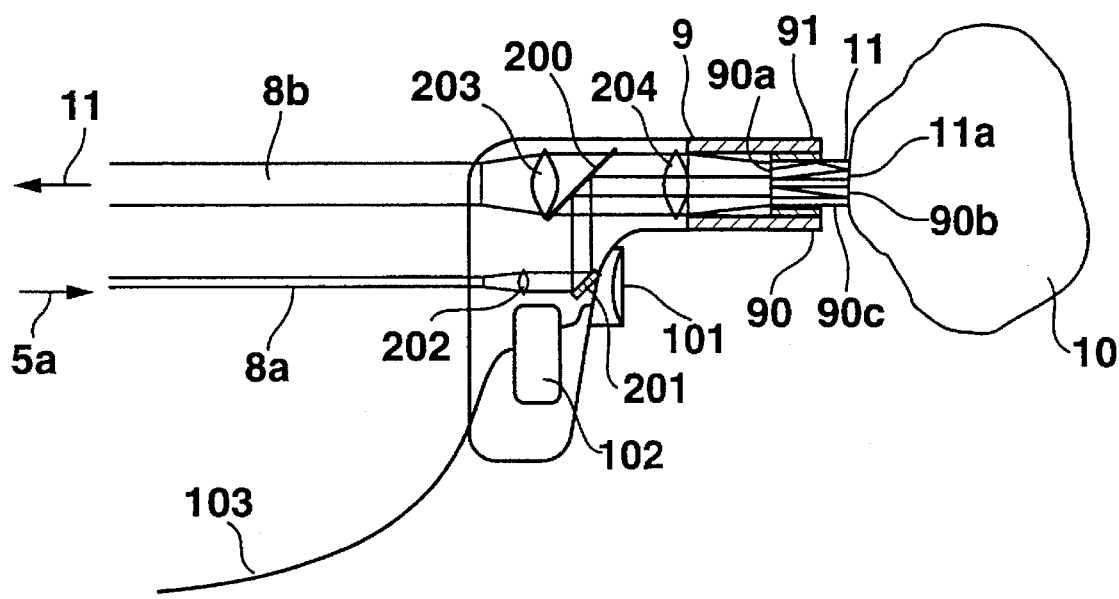
FIG. 6 shows a remote probe with the optical fiber transporting the laser radiation spatially separated from the Raman collecting fiber and with its end imaged onto the first end surface of the transparent element.

As shown in FIG. 6, for other embodiments of the invention the central optical fiber bundle 8a may be separated from the optical fiber bundle 8b. In this case the end surfaces of both partial optical fiber bundles 8a and 8b may be imaged onto the end surface 90a of the transparent optical element. These embodiments may also be combined with the truncated sphere as described in FIG. 5. The reference numbers of FIG. 6 correspond to those of FIG. 2. However, both optical fiber bundles, 8a and 8b, are kept separate. Their end surfaces are both imaged by the lenses 202, 203 and 204 via the planar mirror, 201 and the beam splitter 200 onto the end surface 90a of the planar surface of the transparent element 90.

Figure 7:
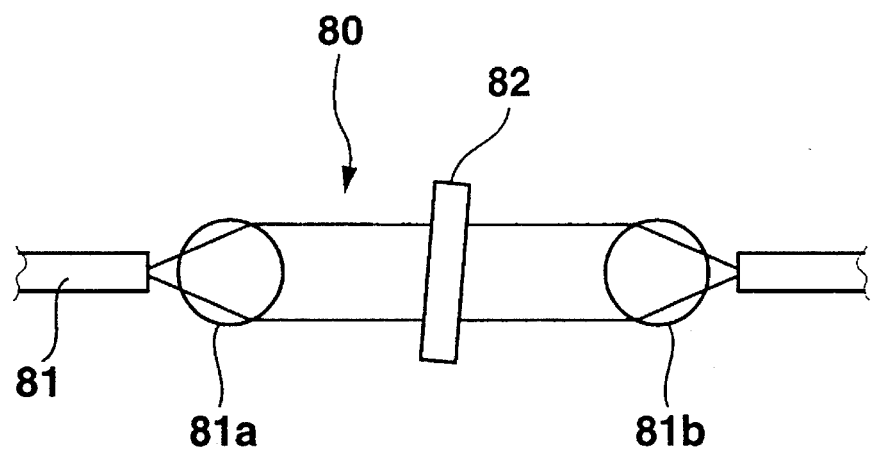
FIG. 7 shows an arrangement of an optical filter to be inserted in the optical fiber, transporting the laser radiation.

FIG. 7 shows in detail a preferred embodiment for the insertion of an optical filter unit 80 into the central optical fiber bundle 8a which is used for the elimination of undesired Raman radiation excited in the fiber material. This insertion should be as near as possible to the collecting element. The central optical fiber bundle is cut. Divergent laser light emerging from the central optical fiber is collimated by a transparent spherical or GRIN (GRadient INdex) element 81. The collimated radiation is transmitted through an optical interference, absorption, or holographic filter 82 which may be inclined relatively to the beam axis for better adjustment as well as for the reduction of back-reflected laser light. Another transparent sphere or GRIN lens focuses the beam into the optical fiber bundle which transports it to the sample. The diameters of the spheres are typically between 2 and 5 mm, of the GRIN lenses between 1 and 2 mm.

The collecting element 9, the switches 101 and 102, and the optical filter unit 80 are preferably integrated in a separate housing, as demonstrated by FIG. 2.

We claim:

1. A Raman spectrometer of the kind having a remote probe, a sample, a laser, and an analysis means, the remote probe comprising:

a first optical fiber means optically connected between the laser and the sample and adapted for transporting laser light to the sample for excitation of a Raman spectrum, the first fiber means comprising an optical filter unit to filter out Raman radiation generated by the laser in the first fiber means;

a second optical fiber means optically connected between the sample and the analysis means and adapted for transporting Raman radiation emitted from the sample to the analysis means to be analysed into the Raman spectrum, the first and the second optical fiber means forming an optical fiber bundle having a planar end surface; and transparent optical means optically connected between the first optical fiber means and the sample and between the second optical fiber means and the sample for concentrating laser light from the first fiber means to a surface of the sample and for collecting and transporting Raman radiation from the sample to the second optical fiber means, the transparent optical means having a first planar surface which is one of attached to and imaged onto the planar end surface of the optical fiber bundle, a second surface adapted for contact to the surface of the sample, and a third enclosing surface which is one of covered with a reflecting coating and adapted as a total reflector, the transparent optical means adapted for connection to and detachment from the planar end surface of the optical fiber bundle.

2. The Raman spectrometer of claim 1, the remote probe further comprising a lateral casing means, the lateral casing means being hollow and cylindrical and having an inner diameter equal to an external diameter of the optical fiber bundle for positioning the lateral casing means over the planar end surface of the optical fiber bundle the inner diameter also being equal to a diameter of the first planar surface, the lateral casing means being adapted to accept the third enclosing surface to fix the transparent optical means at an end of the lateral casing means, whereby the transparent optical means and the lateral casing means are integral with each other and exchangeable.

3. The Raman spectrometer of claim 1, wherein the laser has a wavelength in a near-infrared range.

4. The Raman spectrometer of claim 1, wherein the transparent optical means comprises a material which can be sterilized.

5. The Raman spectrometer of claim 1, wherein the optical fiber bundle is of a Y type.

6. The Raman spectrometer of claim 1, the remote probe further comprising a switch means adapted to activate the laser under manual activation.

7. The Raman spectrometer of claim 6, the remote probe further comprising a gravity switch means adapted to activate the laser only when the remote probe is aimed downwards.

8. The Raman spectrometer of claim 2, wherein the transparent optical means has a shape of one of a truncated cone and a circular cylinder.

9. The Raman spectrometer of claim 1, wherein the transparent optical means has a shape of a paraboloid.

10. The Raman spectrometer of claim 9, wherein the transparent optical means has a shape of a paraboloid with a truncated planar tip.

11. The Raman spectrometer of claim 1, wherein the transparent optical means has a shape of a truncated sphere with two planar parallel surfaces.

12. The Raman spectrometer of claim 1, wherein the transparent optical means comprises a hollow rotationally symmetric inside reflecting element which is open at two axial ends.

13. The Raman spectrometer of claim 1, further comprising at least one of a second and a third transparent optical means, the transparent optical means, the second and the third transparent optical means being exchangeable with each other for alternate use.

14. The Raman spectrometer of claim 13, wherein the transparent optical means, the second transparent optical means and the third transparent optical means are exchangeable, the transparent optical means having a shape of a cylinder, the second transparent means having a shape of a paraboloid, and the third transparent means having a shape of a truncated sphere.

15. The Raman spectrometer of claim 1, wherein the optical filter unit comprises one of two transparent spheres and two GRIN devices for the collimation of light between which an optical filter is optically connected.

16. The Raman spectrometer of claim 15, wherein a surface of the optical filter is not exactly perpendicular to a connecting line between centers of one of the two transparent spheres and the two GRIN devices.

17. The Raman spectrometer according to claim 1, wherein the Raman spectrometer is of the FTIR type.

18. The Raman spectrometer of claim 1, wherein the remote probe further comprises a lateral casing means, the lateral casing means being hollow and cylindrical and having an inner diameter equal to an external diameter of the optical fiber bundle for positioning the lateral casing means over the planar end surface of the optical fiber bundle, the lateral casing means being adapted to accept the third enclosing surface to fix the transparent optical means at an end of the lateral casing means, wherein the remote probe comprises a switch means adapted to activate the laser under manual activation and a gravity switch means adapted to activate the laser only when the remote probe is aimed downwards.

19. The Raman spectrometer of claim 18 further comprising at least one of a second and a third transparent optical means the transparent optical means and the second and third transparent optical means being exchangeable, the transparent optical means having a shape of a cylinder, the second transparent optical means having a shape of a paraboloid, and the third transparent optical means having a shape of a truncated sphere.

20. A Raman spectrometer of the kind having a remote probe, a sample, a laser, and an analysis means for analyzing a Raman spectrum, the spectrometer comprising:

a first optical fiber means optically connected between the laser and the sample and adapted for transporting laser light to the sample for excitation of a Raman spectrum of the sample, the first fiber means comprising an optical filter unit near the sample to filter out Raman radiation generated by the laser in the first fiber means, the optical filter comprising two transparent spheres or two GRIN devices for the collimation of light between which an optical filter is optically connected;

a second optical fiber means optically connected between the sample and the analysis means and adapted for transporting Raman radiation emitted from the sample to the analysis means to be analysed into the Raman spectrum, the first and the second optical fiber means forming an optical fiber bundle having a planar end surface; and transparent optical means optically connected between the first optical fiber means and the sample and between the second optical fiber means and the sample for concentrating laser light from the first fiber means to surface of the sample and for collecting and transporting Raman radiation from the sample to the second optical fiber means, the transparent optical means having a first planar surface which is attached to or imaged onto the planar end surface of the optical fiber bundle, a second surface adapted for contact to the surface of the sample, and a third enclosing surface which is one of covered with a reflecting coating and adapted as a total reflector, the transparent optical means adapted for connection to and detachment from the planar end surface of the optical fiber bundle.

21. A Raman spectrometer of the kind having a remote probe, a sample, a laser, and an analysis means, the spectrometer comprising:

a first optical fiber means optically connected between the laser and the sample and adapted for transporting laser light to the sample for excitation of a Raman spectrum of the sample, the first fiber means comprising an optical filter unit to filter out Raman radiation generated by the laser in the first fiber means, the optical filter unit comprising one to two transparent spheres and two GRIN devices for the collimation of light between which an optical filter is optically connected, wherein a surface of the optical filter is not exactly perpendicular to a connecting line between centers of one of the two transparent spheres and the two GRIN devices;

a second optical fiber means optically connected between the sample and the analysis means and adapted for transporting Raman radiation emitted from the sample to the analysis means to be analysed into the Raman spectrum, the first and the second optical fiber means forming an optical fiber bundle having a planar end surface;

transparent optical means optically connected between the first optical fiber means and the sample and between the second optical fiber means and the sample for concentrating laser light from the first fiber means to a surface of the sample and for collecting and transporting Raman radiation from the sample to the second optical fiber means, the transparent optical means having a first surface which is one of attached to and imaged onto the planar end surface of the optical fiber bundle, a second surface adapted for contact to the surface of the sample, and a third enclosing surface which is one of covered with a reflecting coating and adapted as a total reflector, the transparent optical means adapted for connection to and detachment from the planar end surface of the optical fiber bundle; and a lateral casing means, the lateral casing means being hollow and cylindrical and having an inner diameter equal to an external diameter of the optical fiber bundle for positioning the lateral casing means over the planar end surface of the optical fiber bundle the inner diameter also being equal to a diameter of the first planar surface, the lateral casing means being adapted to accept the third enclosing surface to fix the transparent optical means at an end of the lateral casing means, whereby the transparent optical means and the lateral casing means are integral with each other and exchangeable.

* * * * *